(12) United States Patent
Stone et al.

(10) Patent No.: US 6,962,584 B1
(45) Date of Patent: Nov. 8, 2005

(54) ELECTROMAGNETIC PHOTONIC CATHETER FOR REDUCING RESTENOSIS

(76) Inventors: Gregg W. Stone, 21 Wyckham Hill La., Greenwich, CT (US) 06831; Jeffrey W. Moses, 1175 Park Ave., New York, NY (US) 10128; Martin B. Leon, 875 Park Ave., Apt. 12B, New York, NY (US) 10021; Nicholas N. Kipshidze, 345 E. 80th St., #25B, New York, NY (US) 10021; Harvinder Sahota, 3861 Wisteria St., Seal Beach, CA (US) 90740; Bandula Wijay, 1903 Carrige Creek, Friendswood, TX (US) 77545

( * ) Notice: Subject to any disclaimer, the term of this patent is extended or adjusted under 35 U.S.C. 154(b) by 40 days.

(21) Appl. No.: 10/234,443

(22) Filed: Sep. 4, 2002

Related U.S. Application Data

(60) Provisional application No. 60/317,739, filed on Sep. 6, 2001.

(51) Int. Cl.[7] .............................................. A61B 18/18
(52) U.S. Cl. .................... 606/7; 606/3; 606/15; 607/88; 607/89
(58) Field of Search ........................ 607/88, 89; 606/3, 606/7, 15, 27; 128/898

(56) References Cited

U.S. PATENT DOCUMENTS

| | | | | |
|---|---|---|---|---|
| 5,053,033 A | * | 10/1991 | Clarke | 606/3 |
| 5,417,653 A | * | 5/1995 | Sahota et al. | 604/20 |
| 5,776,174 A | * | 7/1998 | Van Tassel | 607/89 |
| 5,814,039 A | * | 9/1998 | Prescott | 606/7 |
| 5,906,636 A | * | 5/1999 | Casscells et al. | 607/96 |
| 5,908,415 A | * | 6/1999 | Sinofsky | 606/7 |
| 5,997,571 A | * | 12/1999 | Farr et al. | 607/92 |
| 6,200,307 B1 | * | 3/2001 | Kasinkas et al. | 606/7 |
| 6,475,210 B1 | * | 11/2002 | Phelps et al. | 606/7 |

* cited by examiner

*Primary Examiner*—A. Farah
(74) *Attorney, Agent, or Firm*—Kajane McManus

(57) ABSTRACT

The method of vascular treatment for restenosis or vulnerable plaque after an invasive procedure, such as for example angioplasty, stenting with or without drug coating, or drug delivery, comprises: inserting a catheter or hollow guide wire to the treatment location; delivering light through the catheter in the wavelength range of about 700–2500 nm; and moving the light to treat the affected region.

17 Claims, 5 Drawing Sheets

ELECTROMAGNETIC PHOTONIC CATHETER FOR REDUCING RESTENOSIS

CROSS REFERENCE TO RELATED APPLICATIONS

This application claims priority from Provisional Application No. 60/317,739, filed Sep. 6, 2001, of the same title.

FIELD OF INVENTION

The present invention relates to the method of treating tissue in a body cavity to minimize the scar tissue formation, after injury to the tissue by mechanical or by other intervention.

BACKGROUND OF THE INVENTION

When a catheter or other medical device is used in a body cavity, such as an artery, the mechanical rubbing of the catheter, or inflation of the balloon of a balloon angioplasty catheter, or the placement of a stent, can trigger the body to react to such mechanical injury. The body reacts by, among other processes, producing smooth muscle cell and fibroblast migration to the injury site. The body, depending on the location, may also produce endothelial cells and epithelial cells at injury site.

In the case of balloon angioplasty, such reaction by the body will cause a build-up of scar tissue, which can eventually negate the process of angioplasty that was performed in the first place. In other instances, stents are placed in blood vessels to keep the lumen open after angioplasty. The presence of stents, a foreign body, also triggers a set of events for the body to produce smooth muscle cells and causes fibroblast migration to cover-up the struts of the stent, which eventually closes the lumen to a greater or lesser degree.

In addition to the migration of cells, (smooth muscle cells and fibroblasts) another phenomenon that causes closure of vessels after intervention is spasm. Spasm also contributes, more acutely, to the vessel closure resulting, in some instances, to grave consequences.

Many methods have been tried to prevent this process of cell proliferation/migration. In addition to mechanical methods such as stents, various, chemical and combination treatments have been tried.

In the area of drug treatment of the injury site, several inventors have proposed different methods and drugs. Muller, U.S. Pat. No. 5,947,928 suggests a shock wave mechanism to transfer the drug to the needed location. Also, drugs have been embedded or coated in stents for delivery into the vessel wall. Recent results of drug-coated stents have shown some serious draw backs. These include inflammation of the tissue and the presence of "black holes" in the area covered by the stent. Although the exact reason for the black holes is not yet understood, the absence of such black holes in un-coated stents points to the fact the black holes are due to the drug and the coating. Such "black holes" are vacuous areas between the outer surface of the stent and the vessel wall which allow cellular elements to begin to collect there, eventually producing obstruction extending into a lumen of the stent. Although the exact reason for the black holes is not yet understood, the absence of such black holes in un-coated stents points to the fact the black holes are due to the drug and the coating.

Among other treatment methods, laser light has been used in several ways to address the problem. Laser and light treatment has been used in medicine widely both on the skin and outer tissues of the body and inside the body cavity in blood vessels, trachea, lungs and in the gastrointestinal track. The advantage of light and laser is the ability to control the wavelength and the power so that the tissue can absorb the energy at the desired level.

For example, Daikuzono, et. al, U.S. Pat. No. 6,024,738 describes a flexible conduit positioned by a balloon for carrying laser energy for ablating and melting the plaque in arteries.

Pruitt Sr., U.S. Pat. No. 5,993,382 describes a lighted catheter device and an optical fiber delivering light to the desired location by positioning the end of the light fiber between two balloons. Pruitt's main purpose is to illuminate the location of the lesion, and he describes a method to deliver the light energy to the desired location isolated by two occluding balloons. Other methods of delivering laser light, have been described by Ishibashi, U.S. Pat. No. 4,567,882 employing a prism or a bifurcated emitter portion, Ector, U.S. Pat. No. 4,567,882 employing a hemispherical tip formed on the end of the fiber/catheter tip, Mackin, U.S. Pat. No. 4,961,738 using diverging optical fibers, Sugiyama, et al, U.S. Pat. No. 5,036,834 who employed Lens and Kozawa, U.S. Pat. No. 5,335,648 using a mirror to reflect the light energy. Hillsman, U.S. Pat. No. 5,643,251 described a method and apparatus for ablating an obstruction. As is now known in the medical field, laser light ablation produces severe scar tissue and actually compounds the injury caused by mechanical means such as balloons or stents.

Littleford, et. al., U.S. Pat. No. 4,834,073 describes a combination of laser ablation and angioplasty process. Lennox, et. al., U.S. Pat. No. 5,454,807 also describes a method and apparatus, using a light guide, to deliver light and a cooling medium for light irritation.

Most inventors have used light energy in the form of laser and as light to ablate or melt the obstruction or treat the area in way of energy that eventually transforms into energy absorbed by the tissue as heat.

Several complex methods have been adopted to bend the laser light or light using lenses, mirrors etc. so that the treatment area receives the laser light. Various occlusion devices have been used to either centrally locate the laser beam or as means of getting rid of blood and other fluids from the area of treatment. Many have attempted to use a cooling fluid to cool the area of treatment to avoid thermal injury.

All these methods are complex in nature and quite difficult to practice. Occlusion devices stop the blood flow to the organ thereby producing ischemic manifestations in the organ.

Another major vascular disease that affects a large number of patients is vulnerable plaque. Vulnerable plaque can be described as atherosclerotic plaque containing a lipid pool, which is covered by a thin fibrous capsule over a layer of collagen and elastin that gives tensile strength to this exracellular matrix. The fibrous capsule typically is a single layer of endothelial cells, which may be eroded by both inflamatatory T-Lymphocytes and invading smooth muscle cells. Activated macrophages moving into the plaque from the vasa vasorum produce protelytic enzymes that promote collagen degradation causing cap disruption and thrombogenic surface activation associated with acute coronary syndromes. The capsule is quite unstable and when ruptured due to various causes release the lipids to the blood stream, which causes clotting. The clots so formed can be instrumental in causing a myocardial infarction or heart attack when the arteries involved are the coronary arteries.

Several inventors have developed means to identify and diagnose the existence of vulnerable plaque. Moreno et. al. in Patent Application 20010047137 describes the use of a fiber optic device carrying light in the wave length rage from 1400–4100 nm as means of identifying such plaque. Casscells and Willerson in U.S. Pat. No. 5,906,636 describe a method in identifying and heating the cells with a catheter using infrared radiation. They describe that the cells are heated for a sufficient period of time (15–60 minutes) and at sufficient temperature (41–44 Degrees Centigrade) to induce programmed cell death. Speras in U.S. Pat. No. 4,799,479 also describes a similar concept of heating the plaque using thermal means to achieve the same objective.

BRIEF SUMMARY OF THE INVENTION

The present invention pertains to the method of reducing the body's reaction to mechanical injury and the vulnerable plaque and an apparatus for accomplishing such method.

More particularly, the present invention describes a non thermal means and a fiber optic catheter to deliver certain wavelength light, coherent or non-coherent, of certain power to reduce the proliferation of smooth muscle cells, migration of fibroblasts, while enhancing the growth endothelial cells as well as means of stabilizing the fibrous cap of vulnerable plaque. More particularly the present invention describes the use of near infrared energy in the preferred wavelength range between 750–2500 nm either ultra short, short, pulsed or continuous at preferred power levels between 100–1000 milli-joules/cm2. A wavelength between 800–950 nm is found to be more effective. Although other power levels are applicable to the present invention, these power levels cause minimum thermal damage, if any, to the tissue being irradiated.

In the present invention, near infrared light either in its coherent form such as from an infrared laser source or non-coherent form such as from a infrared diode is used along with a fiber optic delivery system. The catheter tip is moved back and forth to irradiate the desired length of the lesion and when necessary it can be manually or mechanically rotated to cover the length of the lesion.

In the power range aforementioned, of the infrared source, no cooling medium is necessary which can complicate the delivery device and make such device bulky.

It is also not necessary to use an occlusion device such as a balloon to get rid of blood, as infrared radiation can travel through blood medium as compared to other wavelengths of light.

Although centering methods are described in the invention, such centering is not mandatory in treating the lesions in small blood vessels (2–5 mm), as the diameters are small.

As the treatment is done while blood is flowing in the case of a blood vessel, any cooling needed will be accomplished by the flowing blood as, in the range of power used, the heat generated is minimal. Additionally no specific "light bending" is needed, as the infrared radiation will be scattered due to the colloidal nature of blood. Some methods to enhance scattering is described, however are not an essential requirement, and simplicity is preferred to make the device less costly.

DETAILED DESCRIPTION OF THE DRAWINGS

FIGS. 4 and 4a show an alternative centering feature to FIGS. 3 and 3a.

DESCRIPTION OF PREFERRED EMBODIMENT

Figure 1:
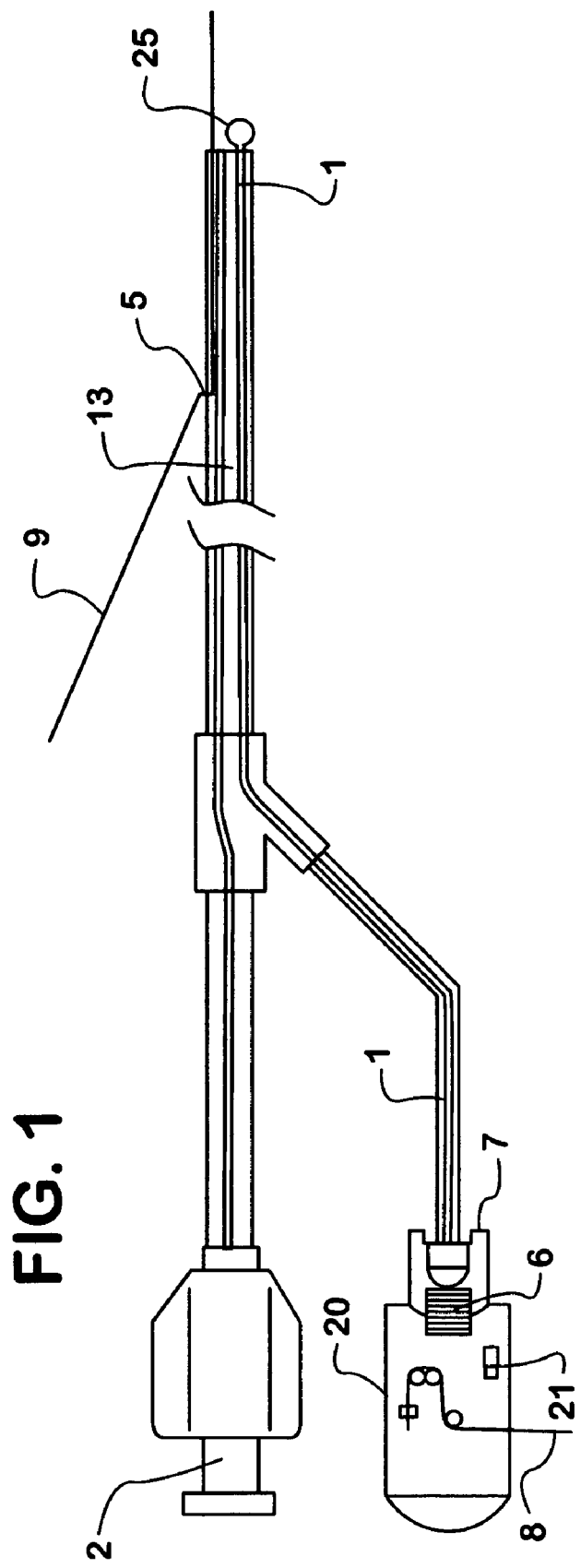
FIG. 1 is an elevational view of the catheter of the present invention.

The preferred catheter is made from extruded plastic tube having a lumen to carry a fiber optic fiber or a bundle of optical fibers (1) in its entire length or part thereof. The fiber optic fiber is connected to a universal connector (UC) at the proximal end 7. An infrared source 6 is connected to the universal connector securely during irradiation. The infrared source is of a preferred wavelength between 700 and 2500 nanometer. The infrared source can be continuous or pulsed. Pulsing the infrared energy source will enable control of the power level delivered to the lesion. Pulsing can be accomplished by any one of different means of electrical circuitry.

To advance the catheter to the desired lesion location, a guide wire (9) is used in the guide wire lumen 18. The same lumen can be used to flush the catheter if necessary. The catheter is threaded over the guidewire in the usual manner common to interventional procedures. The guide wire lumen has an opening 5 so that the guidewire exits at this location. In this design option the catheter can be used as a rapid exchange catheter, whereby the catheter can be introduced or withdrawn without having to remove the guidewire.

In the same design the guide wire can exit the hub 2 in which case the catheter can be used as an over the wire (OTW) catheter. The same lumen can be used to infuse fluids or drops, if necessary.

The safety band 8, which is a insulating tab placed between two electrical conductors 20 that enable the completion of the electrical circuit is made a part of this design so that the device cannot be accidentally switched on by pressing/sliding the power on switch 21.

In the normal use of this device the infrared catheter is advanced either over a guidewire, in the OTW mode, or in the rapid exchange mode to lesion area. Depending on the degree of irradiaion required the infrared unit could be placed to a continuous or pulsed wave mode. The safety ribbon 8 is pulled and removed making electrical contact. The power switch enabling the infrared radiation is then activated. The catheter is then moved up and down the lesion area for a period of time, typically for 2–3 seconds to irradiate the lesion with infrared radiation. In certain lesions more time may be needed to provide sufficient radiation to prevent re-stenosis. The catheter is then removed after radiation and discarded.

Alternative tip design for the catheter has a portion of the distal end of the fiber optic fiber roughened, using an abrasive paper or similar device. A section 3–5 mm long outer surface of the optic fiber is roughened to provide scatter of the infrared radiation laterally or by providing a transparent spherical shape at the end of the catheter tip to reflect the coherent infrared radiation perpendicular to the axis of the fiber optic fiber.

Figures 2, 2A, 2B:
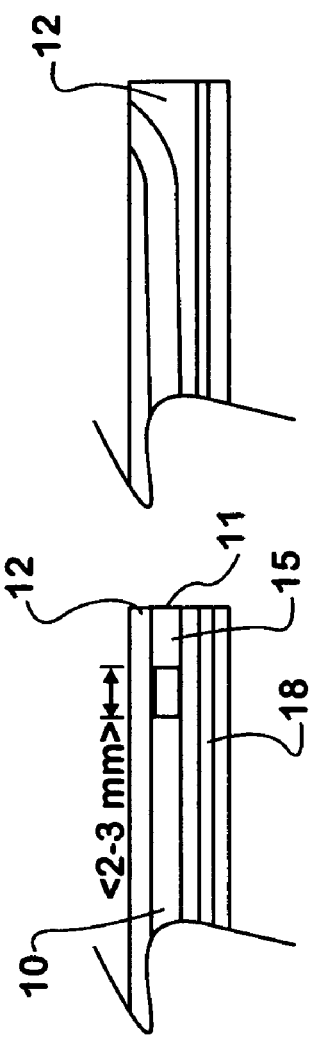
FIGS. 2, 2A and 2B are alternative embodiments to FIG. 1.

In another embodiment the optic fiber is 1–2 mm short of the distal end of the catheter tube as shown in FIG. 2. A separate piece of plastic material 11 is bonded to the catheter tip distal to the optic fiber 10. The optic fiber can be a one single optic fiber or an optic fiber bundle where the distal end of the fiber is placed within 1–2 mm from the distal end of the catheter tube and can be staggered to facilitate scattering of infrared energy.

The infrared radiation is scattered by the plastic element 11. Furthermore, minute particles typically metallic or other reflective flakes 15 can be provided in the scattering element 11, which is bonded to the distal end of the catheter 12. In these instances the catheter tube is preferably made from a transparent plastic. As shown in FIG. 2A, it is also possible to have the fiber optic exit at an angle through a hole cut in tube 12 so that the fiber is directed towards the vessel wall. The exit can be at any angle. The beam will impact the wall closer to the tip of the catheter if the angle is about 45 degrees to the axis of the catheter. The fiber is terminated at the outer diameter of the catheter so that the fiber is flush with its surface. Further, as shown in FIG. 2B, a spherical head 25 may be provided for the fiber optic to produce a desired degree of angulated delivery of light from such spherical head 25.

A stiffener wire 13, (in FIG. 1) which typically is tapered, is placed next to the optic fiber, for the entire length of the catheter or part thereof to impart column strength to the catheter, which will enhance pushability.

Figures 3, 3A:
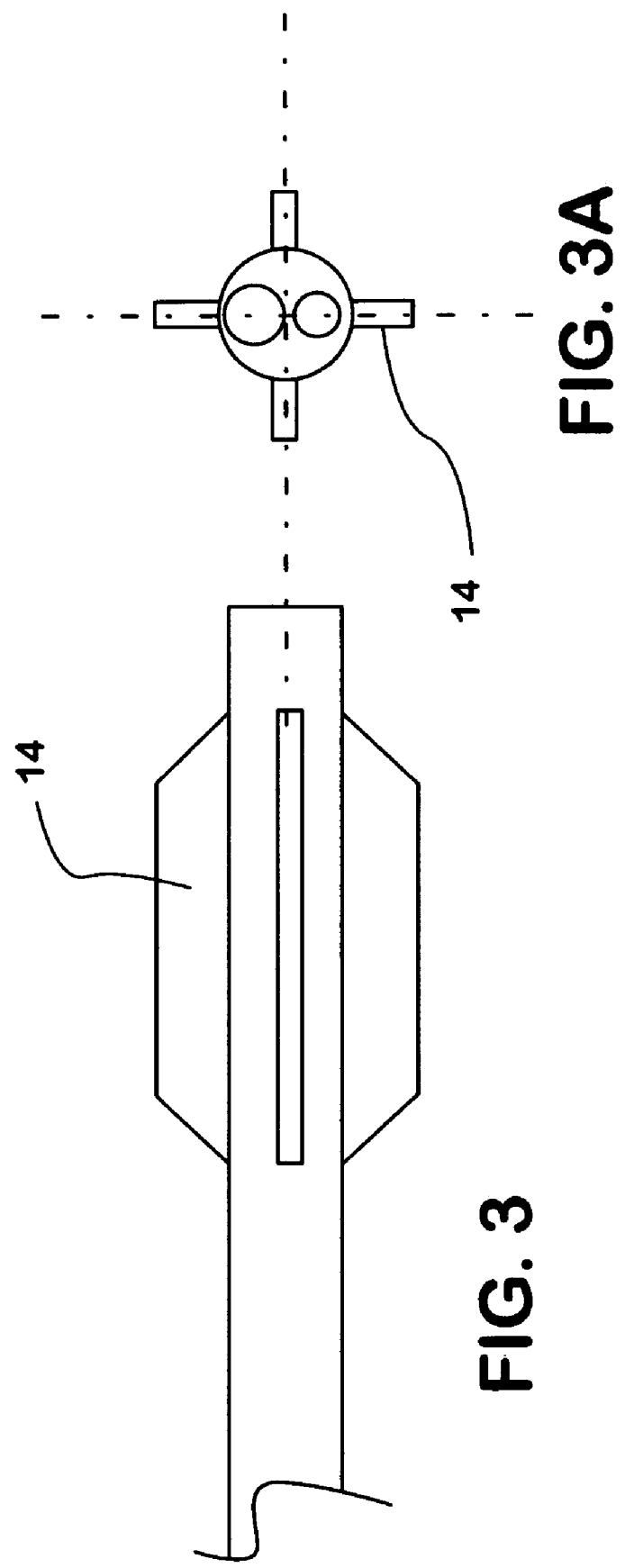
FIGS. 3 and 3a show the centering feature.

A variation of centering devices can be adopted to center the catheter, so that the radiation is uniform and symmetrical. The preferred embodiment, as shown in FIG. 3, is one that has flutes 14, at the distal region close to the end of the catheter. These flutes can be arranged circumferentially so that the catheter is central. The flutes can be of a soft plastic such as PEBAX, Polyurethane, and Polyethylene etc. or can also be from pre-shaped Ni-Ti alloys struts commonly known as Nitinol.

Figure 4:
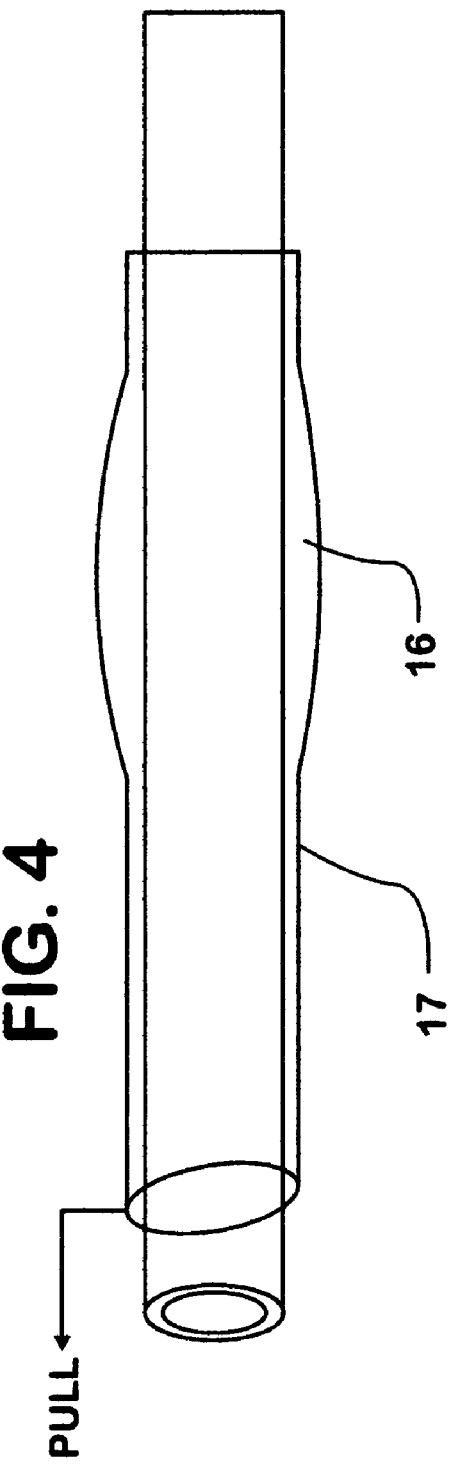
Figure 4A:
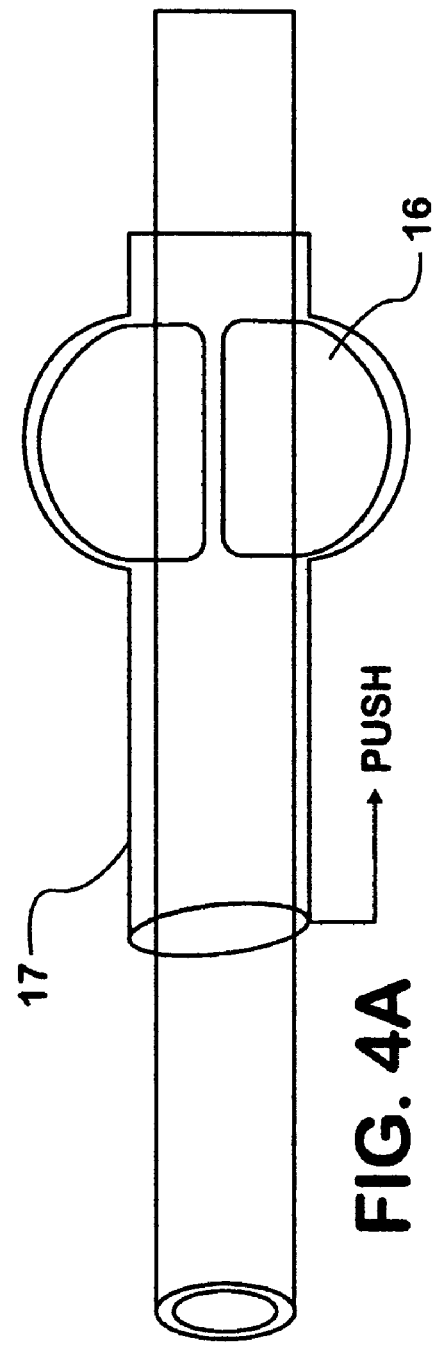

Another variation is to provide "wings" 16 that can be expanded and retracted so that the infrared radiation catheter can be advanced through a guiding catheter and spread the wings in order to center the catheter. Such an embodiment is described in FIG. 4. In this embodiment the outer sleeve contains at least two members 16 that expand out when the outer tube 17 is pushed forward and collapse when the outer tube is pulled. As such in this design the infrared radiation catheter can be advanced through a larger catheter, a guiding catheter, (not shown) to the proper location and prior to the activation of radiation the outer tube is pushed forward to centralize the catheter tip and subsequently radiation is applied.

The advantage of the flute structures is that during this process the blood flow is not impaired when radiating lesions in blood vessels, and blood can be used as a scattering medium for the radiation.

Figure 5:
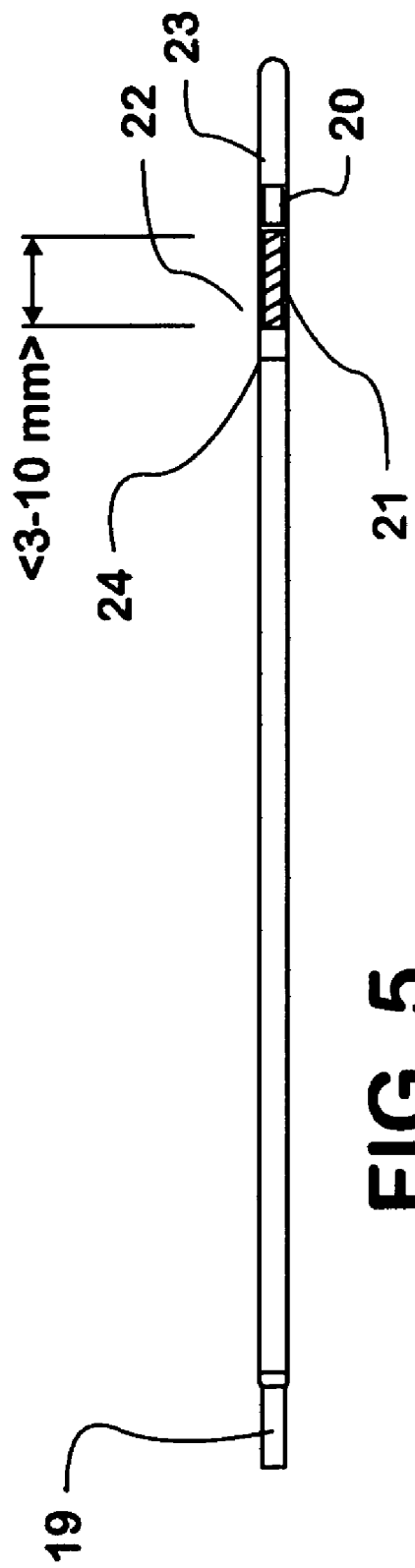
FIG. 5 is a view showing the use of a guide wire.

The radiation can also be provided by means of a guidewire that is advanced to the lesion post angioplasty. Such a device is shown in FIG. 5. In FIG. 5, the optic fiber is placed inside a tube, plastic or metal, and continues until the tip of the optic fiber is under the window 22. The distal portion of the guide wire is bonded to the proximal shaft at 24. The distal portion is either made of flexible plastic or a spirally wound metal coil. At 22 the coil is spread apart so that a window is formed. To keep the integrity of the wire intact a safety sleeve is placed inside the coil but over the tip of the fiber optic. A reflector piece similar to the one described earlier in FIG. 2, item 11 is placed to provide the scattering of the radiation. The coil is spread for a distance of 3–10 mm for the radiation to escape.

What is claimed is:

1. A method of vascular treatment for restenosis or vulnerable plaque after an invasive procedure, such as for example angioplasty, stenting with or without drug coating, or drug delivery, the steps of the method consisting of:
   inserting a catheter or hollow guide wire to the treatment location;
   supplying power to a light source thereby generating light in the fluence range of about 100–1000 milli-joules/cm$^2$;
   delivering light from said light source through said catheter in the wavelength range of about 700–2500 nm;
   using at least one optic fiber to deliver said light;
   configuring the distal end of said guide wire from plastic or a metal coil;
   keeping the windings of said metal coil separated to create a window to allow said light to exit;
   extending said fiber beyond a distal end of said catheter or guide wire;
   roughening said extend led fiber to improve light dispersion; and
   moving said light to treat the affected region.
2. The method of claim 1, comprising:
   pulsing the delivered light on and off.
3. The method of claim 1, comprising:
   allowing blood to flow as said light is delivered.
4. The method of claim 3, comprising:
   using said flowing blood to disperse said light.
5. The method of claim 3, comprising:
   using said flowing blood to remove generated heat from said light.
6. The method of claim 1, comprising:
   extending said fiber beyond a distal end of said catheter or guide wire; and
   providing a rounded terminal on said extending fiber to improve light dispersion.
7. The method of claim 1, comprising:
   configuring said catheter for delivery in an over the wire manner.
8. The method of claim 1, comprising:
   configuring said catheter for delivery in a rapid exchange manner.
9. The method of claim 1, comprising:
   using a laser or a diode as the source of said light.
10. The method of claim 9, comprising:
    providing a sleeve over said optic fiber and below said coil to protect said optic fiber.
11. A method of vascular treatment for restenosis or vulnerable plaque after an invasive procedure, such as for example angioplasty, stenting with or without drug coating or drug delivery the steps of the method consisting of:
    inserting a catheter or hollow guide wire to the treatment location;
    supplying power to a light source thereby generating light in the fluence range of about 100–1000 milli-joules/cm$^2$;
    delivering light from said light source through said catheter in the wavelength range of about 700–2500 nm;
    using at least one optic fiber to deliver said light;
    configuring the distal end of said guide wire from plastic or a metal coil;
    keeping the windings of said metal coil separated to create a window to allow said light to exit;
    allowing said optic fiber to end laterally before the distal end of the catheter;
    roughening said fiber to improve light dispersion; and
    moving said light to treat the affected region.
12. The method of claim 11, comprising:
    terminating the optic fiber before the end of said catheter or guide wire;
    providing a tip beyond the distal end of said optic fiber; and
    dispersing said light with said tip.

13. The method of claim 12, comprising:
forming said tip from a plastic material.

14. The method of claim 13, comprising:
embedding particles to disperse said light in said plastic material.

15. A method of vascular treatment for restenosis or vulnerable plague after an invasive procedure, such as for example angioplasty, stenting with or without drug coating, or drug delivery, the steps of the method consisting of:
   inserting a catheter or hollow guide wire to the treatment location,
   supplying power to a light source thereby generating light in the fluence range of about 100–1000 milli-joules/$cm^2$;
   derivatives light from said light source through said catheter in the wavelength range of about 700–2500 nm:
   using at least one-optic fiber to deliver said light;
   configuring the distal end of said guide wire from plastic or a metal coil;
   keeping the windings of said metal coil separated to create a window to allow said light to exit;
   extending said fiber beyond a distal end of said catheter or guide wire;
   roughening said extended fiber to improve light dispersion;
   providing a positioning device on the outside of said catheter or guide wire that allows blood to continue circulating; and
   moving said light to treat the affected region.

16. The method of claim 15, comprising:
   retracting said positioning device during placement of said catheter or guide wire;
   extending said positioning device when said catheter or guide wire is in the desired location.

17. The method of claim 16, comprising:
   providing said positioning device as a collapsible sleeve having a plurality of openings spanned by thin strips;
   collapsing said sleeve to bow out said strips to position said catheter or guide wire.

* * * * *